US011155849B2

(12) United States Patent
Baek et al.

(10) Patent No.: US 11,155,849 B2
(45) Date of Patent: Oct. 26, 2021

(54) IMP-PRODUCING MICROORGANISM AND METHOD OF PRODUCING IMP USING THE SAME

(71) Applicant: CJ CHEILJEDANG CORPORATION, Seoul (KR)

(72) Inventors: Min Ji Baek, Suwon-si (KR); Baek Seok Lee, Seoul (KR); Ji Hye Lee, Anyang-si (KR); Nara Kwon, Yongin-si (KR); Ju Jeong Kim, Suwon-si (KR); Jin Man Cho, Seongnam-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/346,418

(22) PCT Filed: Dec. 14, 2018

(86) PCT No.: PCT/KR2018/015935
§ 371 (c)(1),
(2) Date: Apr. 30, 2019

(87) PCT Pub. No.: WO2019/117671
PCT Pub. Date: Jun. 20, 2019

(65) Prior Publication Data
US 2020/0377917 A1 Dec. 3, 2020

(30) Foreign Application Priority Data
Dec. 15, 2017 (KR) .................. 10-2017-0173504

(51) Int. Cl.
*C12P 19/32* (2006.01)
*C12N 1/20* (2006.01)
*C12N 15/10* (2006.01)
*C12R 1/15* (2006.01)

(52) U.S. Cl.
CPC ............... *C12P 19/32* (2013.01); *C12N 1/20* (2013.01); *C12N 1/205* (2021.05); *C12N 15/1034* (2013.01); *C12R 2001/15* (2021.05)

(58) Field of Classification Search
CPC ....... C12P 19/32; C12N 1/20; C12N 15/1034; C12N 15/77; C12R 2001/15; C07K 14/34
See application file for complete search history.

(56) References Cited

U.S. PATENT DOCUMENTS

| 7,767,626 B2 | 8/2010 | Toriyabe et al. |
| 9,271,500 B2 | 3/2016 | Takahashi et al. |
| 9,783,509 B2 | 10/2017 | Alig et al. |
| 9,802,930 B1 | 10/2017 | Tanabe et al. |
| 9,924,719 B2 | 3/2018 | Tanabe et al. |
| 10,039,282 B2 | 8/2018 | Kohler et al. |

FOREIGN PATENT DOCUMENTS

| EP | 3 608 410 A1 | 2/2020 |
| JP | 2-88570 A | 3/1990 |
| KR | 2003-0042972 A | 6/2003 |
| KR | 10-2007-0060207 A | 6/2007 |
| KR | 10-2007-0060208 A | 6/2007 |
| KR | 10-2010-0109732 A | 10/2010 |
| KR | 10-1744958 B1 | 6/2017 |
| WO | 99/55668 A1 | 11/1999 |
| WO | 2010/100189 A1 | 9/2010 |
| WO | 2013/191113 A1 | 12/2013 |
| WO | 2015/004028 A1 | 1/2015 |
| WO | 2015/091267 A1 | 6/2015 |
| WO | 2016/052247 A1 | 4/2016 |
| WO | 2016/052455 A1 | 4/2016 |

OTHER PUBLICATIONS

GenBank Accession No. AB0675, probable multidrug efflux STY1517 [imported] *Salmonella enterica* subsp. *enterica* serovar Typhi (strain CT18) 2 pages, Nov. 18, 2002.
Parkhill et al., "Complete genome sequence of a multiple drug resistant *Salmonella enterica* serovarTyphi CT18," *Nature* 413:848-852 (2001).
Kisselev, "Polypeptide Release Factors in Prokaryotes and Eukaryotes: Same Function, Different Structure," *Structure* 10:8-9 (2002).
Whisstock et al., "Prediction of protein function from protein sequence and structure," *Quarterly Reviews of Biophysics* 36(3):307-340 (2003).
Witkowski et al., "Conversion of a β-Ketoacyl Synthase to a Malonyl Decarboxylase by Replacement of the Active-Site Cysteine with Glutamine," *Biochemistry* 38:11643-11650 (1999).
U.S. Appl. No. 16/346,041, filed Apr. 29, 2019, Novel Polypeptide and Method of Producing IMP Using the Same.
U.S. Appl. No. 16/425,897, filed May 29, 2019, Novel Polypeptide and Method of Producing IMP Using the Same.
U.S. Appl. No. 16/346,725, filed May 1, 2019, Novel Polypeptide and Method of Producing IMP Using the Same.
Peifer et al., "Metabolic engineering of the purine biosynthetic pathway in Corynebacterium glutamicum results in increased intracellular pool sizes of IMP and hypoxanthine," Microbial Cell Factories, 11:138, 2012, 14 pages.
GenBank Accession No. WP_066795119, retrieved May 24, 2019, from https://www.ncbi.nlm.nih.gov/protein/WP_066795119.1/.
GenBank Accession No. WP_066795121, retrieved May 24, 2019, from https://www.ncbi.nlm.nih.gov/protein/WP_066795121.1/.

(Continued)

Primary Examiner — Paul J Holland
(74) Attorney, Agent, or Firm — Seed IP Law Group LLP

(57) ABSTRACT

The present disclosure relates to a microorganism of the genus *Corynebacterium* producing 5'-inosine monophosphate, with an enhanced activity of an IMP export protein; a method for preparing 5'-inosine monophosphate using the same; a composition for producing 5'-inosine monophosphate; and a method for increasing export of 5'-inosine monophosphate.

4 Claims, No Drawings
Specification includes a Sequence Listing.

(56) References Cited

OTHER PUBLICATIONS

Ishii et al., "Improved Inosine Production and Derepression of Purine Nucleotide Biosynthetic Enzymes in 8-Azaguanine Resistant Mutants of Bacillus subtilis," Agr. Biol. Chem. 36(9):1511-1522 (1972).
MFS transporter [Corynebacterium stationis]—GenBank: AMJ44984.1, Feb. 16, 2016.
GenBank: ASJ19118.1, "transcriptional regulator [Corynebacterium stationis]," (two pages) Jul. 5, 2017.
Mori et al., "A novel process of inosine 5'-monophosphate production using overexpressed guanosine/inosine kinase," Appl Microbiol Biotechnol, 48:693-698, 1997, 6 pages.
NCBI Reference Squence WP_066795119.1, retrieved from https://www.ncbi.nlm.nih.gov/protein/1055045151/ on May 23, 2019.
NCBI Reference Sequence WP_066795121.1, retrieved from https://www.ncbi.nlm.nih.gov/protein/WP_066796121.1/ on May 24, 2019.
Adrio et al., "Genetic improvement of processes yielding microbial products," *FEMS Microbiol Rev 30*:187-214 (2006).
Ledesma-Amaro et al., "Biotechnological production of feed nucleotides by microbial strain improvement," *Process Biochemistry*, http://dx.doi.org/10.1016/j.procbio.2013.06.025, 8 pages (2013).
Sanchez et al., "Metabolic regulation and overproduction of primary metabolites," *Microbiol Biotechnology 1*(4):283-319 (2008).

SEQUENCE LISTING

```
<160> NUMBER OF SEQ ID NOS: 31

<210> SEQ ID NO 1
<211> LENGTH: 222
<212> TYPE: PRT
<213> ORGANISM: Unknown
<220> FEATURE:
<223> OTHER INFORMATION: ImpE1

<400> SEQUENCE: 1

Leu His Ala Val Gln Glu Val Asn Asp Asn Glu Glu Asp Ser Leu Pro
1               5                   10                  15

Gly Ser Asp Leu Gly Leu Arg Glu Gln Lys Arg Leu Ala Thr Lys His
            20                  25                  30

Arg Ile Glu Asp Ala Ala Thr Arg Leu Val Asp Glu Ser Ser Phe Asp
        35                  40                  45

Lys Val Thr Ile Glu Glu Ile Cys Glu Ala Ala Gly Ile Ser Arg Arg
    50                  55                  60

Thr Phe Phe Asn Tyr Phe Ser Thr Lys Glu Ser Ala Val Ile Gly Ala
65                  70                  75                  80

Ser Ser Glu Pro Leu Thr Glu Lys Gln Arg Asn Asp Phe Leu Asn Ala
                85                  90                  95

Asp Ala Ser Asn Leu Leu Gln Leu Met Val Glu Gln Ile Lys Gln His
            100                 105                 110

Leu Glu Ser Ser His Gln Ser Gln Ala Ile His Asp Arg Arg Gln Arg
        115                 120                 125

Ile Phe Ala Asp Pro Asp Val Ala Val Arg Ala Met Ala Phe Arg Lys
    130                 135                 140

Glu Arg Ser Arg Glu Thr Met Glu Leu Ile Ala Gln Arg Leu Arg Glu
145                 150                 155                 160

His Pro Glu Glu Gln Arg Ala Pro Glu Leu Asp Pro Glu Thr Glu Ala
                165                 170                 175

Met Leu Leu Ser Gly Phe Ile Arg Glu Ala Thr Trp Met Ala Ile Ser
            180                 185                 190

Arg Pro Asp Arg Asp Cys Ala Leu Pro Val Gly Asp Arg Ile Tyr Arg
        195                 200                 205

Ala Met Glu Leu Val Lys Asn Tyr Thr Lys Gly Leu Glu Trp
    210                 215                 220

<210> SEQ ID NO 2
<211> LENGTH: 549
<212> TYPE: PRT
<213> ORGANISM: Unknown
<220> FEATURE:
<223> OTHER INFORMATION: ImpE2

<400> SEQUENCE: 2

Met Val Ala Lys Asn Ser Thr Pro Ser Thr Ala Gly His Ala Ser Ala
1               5                   10                  15

His Thr Ala Glu Glu Phe Pro Val Ala Asn Ala Glu Met Ala Thr Pro
            20                  25                  30
```

-continued

```
Ser Ala Ile Asp Pro Asn His Gly Lys Lys Thr Ala Asp Asn Val Gly
         35                  40                  45

Ile Ile Phe Ala Ala Leu Met Leu Thr Met Leu Met Ser Ser Leu Gly
 50                  55                  60

Gln Met Ile Phe Gly Ser Ala Leu Pro Thr Ile Val Gly Glu Leu Gly
 65                  70                  75                  80

Gly Val Asp Gln Met Ser Trp Val Ile Ser Ala Phe Met Val Thr Met
                 85                  90                  95

Thr Ile Ala Met Pro Leu Ala Gly Gln Leu Gly Asp Arg Met Gly Arg
                100                 105                 110

Lys Trp Val Tyr Ile Ser Gly Ile Ser Ile Phe Val Ile Gly Ser Thr
                115                 120                 125

Leu Gly Gly Phe Ala Asn Gly Met Gly Met Leu Ile Thr Gly Arg Ala
        130                 135                 140

Ile Gln Gly Phe Gly Ala Gly Ile Met Met Ile Ser Ser Gln Ser Ile
145                 150                 155                 160

Val Ala Glu Val Val Ser Ala Arg Glu Arg Gly Lys Phe Met Gly Ile
                165                 170                 175

Met Gly Gly Val Phe Gly Val Ser Ser Val Leu Gly Pro Val Leu Gly
        180                 185                 190

Gly Trp Phe Thr Asp Gly Pro Gly Trp Arg Trp Gly Leu Trp Ile Asn
        195                 200                 205

Ile Pro Leu Gly Leu Leu Ala Ile Ile Val Cys Ala Phe Val Leu Lys
210                 215                 220

Leu Arg Val Gly Glu Gln Gly Phe Lys Gly Phe Asp Trp Met Gly Phe
225                 230                 235                 240

Ala Ala Ile Ala Ile Thr Thr Ser Thr Leu Ile Leu Leu Thr Thr Trp
                245                 250                 255

Gly Gly Ser Glu Tyr Glu Trp Thr Ser Pro Thr Ile Leu Ser Met Ala
        260                 265                 270

Ala Val Val Ile Val Gly Ala Leu Leu Thr Val Phe Ile Glu Ser Arg
        275                 280                 285

Ala Ser Gln Pro Leu Ile Pro Val Gln Leu Phe Lys Asn Arg Asn Met
        290                 295                 300

Val Leu Thr Thr Leu Ala Gly Thr Val Leu Gly Leu Ala Met Met Gly
305                 310                 315                 320

Val Leu Gly Tyr Met Pro Thr Tyr Leu Gln Met Val His Thr Leu Thr
                325                 330                 335

Pro Thr Glu Ala Gly Leu Met Met Ile Pro Met Met Val Gly Met Ile
                340                 345                 350

Gly Val Ser Thr Gly Val Gly Phe Ile Ile Ala Lys Thr Gly Asn Tyr
        355                 360                 365

Lys Tyr Tyr Pro Ile Ala Gly Leu Ala Ile Thr Ala Phe Ala Leu Trp
        370                 375                 380

Trp Met Ser Gln Met Thr Val Glu Thr Ser Leu Thr Gly Ile Gly Val
385                 390                 395                 400

Arg Phe Leu Val Phe Gly Val Gly Leu Gly Phe Val Met Gln Val Leu
                405                 410                 415

Val Leu Ile Val Gln Asn Ser Phe Pro Val Ser Gln Val Gly Thr Ala
                420                 425                 430

Thr Ala Ala Asn Asn Phe Phe Arg Gln Ile Gly Ser Ala Leu Gly Ala
        435                 440                 445

Ser Ile Val Gly Ser Met Phe Ile His Asn Met Gln Asn Glu Met Ala
```

```
            450                 455                 460
Thr Arg Leu Pro Asp Ala Leu Ala Ser Leu Gly Lys Glu Gly Ala Ala
465                 470                 475                 480

Ile Ser Gln Gln Phe Gln Gly Ala Asp Ala Ala Asn Ser Leu Thr Pro
                485                 490                 495

His Ala Val Ala Glu Leu Pro Asp Val Leu Arg Asp Ala Ile Leu Asn
            500                 505                 510

Ser Tyr Asn Asp Gly Leu Thr Pro Val Ile Gly Met Met Val Pro Leu
        515                 520                 525

Ala Ile Val Ala Met Leu Ile Leu Phe Pro Leu Arg Gln Glu Arg Leu
    530                 535                 540

Lys Glu Thr Ile Glu
545

<210> SEQ ID NO 3
<211> LENGTH: 2312
<212> TYPE: DNA
<213> ORGANISM: Unknown
<220> FEATURE:
<223> OTHER INFORMATION: impE1E2

<400> SEQUENCE: 3
ttgcatgctg tgcaagaagt taatgacaat gaagaagact ccctccctgg cagtgacctc      60
gggttaaggg agcagaagcg attggcaacc aagcatcgca tcgaagacgc cgcgacacgg     120
ttggttgatg aatcgagctt tgacaaagta acaattgaag aaatttgcga agccgccggg     180
atttcccgac gcacctttt taattatttc agcacgaaag aaagcgccgt tattggcgcg     240
tcctcggaac cgttgacgga aaagcaacgc aatgacttct gaatgctga cgccagcaat     300
ctcctgcagc tgatggttga gcagatcaaa aacacttgg agtcttctca ccagagtcaa     360
gcgattcacg accgtcgtca gcgaatcttt gcggatccgg atgtcgcggt acgtgcaatg     420
gcgtttcgca aggaacgctc acgggaaacc atggagctaa tcgctcaacg tcttcgggag     480
catcctgaag aacaacgcgc cccagaattg gatccggaaa cagaggcgat gctgctgagc     540
ggattcattc gcgaagccac ctggatggct atctcacgac ccgatcgtga ttgtgcactg     600
ccagtgggtg accgcatcta tcgcgcgatg gaattggtaa agaattacac gaaaggactg     660
gaatggtagc taaaaactcc accccaagca cggccggcca cgccagtgct cacactgcgg     720
aagaattccc agtggccaat gctgaaatgg caacgccttc agcaatcgac ccaaaccacg     780
gtaaaaagac cgcggataac gtcggcatta tcttcgctgc cttgatgctc accatgctga     840
tgagctcttt ggggcagatg attttcggtt ccgctctgcc aaccatcgtc ggcgagctcg     900
gcggcgtgga ccagatgagc tgggtaattt cagcatttat ggtcaccatg accattgcta     960
tgccactagc cggtcagctc ggtgaccgca tgggccgcaa gtgggtctac atctcaggta    1020
tctccatttt cgttattggc tcgacgctcg gtgctttgc caatggcatg gcatgctga    1080
tcaccggacg tgcaatccag ggcttcggtg ccggcatcat gatgatttcc tcgcagtcga    1140
ttgtggctga ggttgtctcc gcacgtgagc gcggcaagtt catgggtatt atgggcggcg    1200
tctttggcgt ctcctccgta ctgggtccag ttctcggtgg ctggttcacc gatggtcccg    1260
gttggcgttg gggcctgtgg atcaacattc cactgggtct gctggcaatt attgtctgcg    1320
ctttcgtact gaagctgcgc gtgggcgagc aagctttaa gggctttgac tggatgggtt    1380
ttgcggccat cgcaatcacg accagcaccc tgattctgct caccacttgg ggcggaagcg    1440
aatacgagtg gacttcccca actattttgt ccatggctgc cgtagtcatc gtcggcgcgc    1500
```

```
tgctcaccgt gttcattgag tcgcgtgcat cccagccgct gatcccggtt cagctattta    1560
agaaccgcaa catggttttg accaccctcg ccggtactgt tttgggtctg gccatgatgg    1620
gcgtgctcgg ctacatgcca acctacctgc agatggtgca caccctgacg ccaactgaag    1680
caggcttgat gatgatcccg atgatggtcg gcatgatcgg tgtctccact ggtgttggct    1740
tcatcatcgc taagaccggc aactacaagt actaccccat cgcgggcctg gccatcacgg    1800
cgtttgcttt gtggtggatg tcccagatga ccgttgagac ttcattgacc ggtatcggag    1860
ttcgcttcct tgtattcggt gtcggcttgg gctttgtcat gcaggtactg gtgctgattg    1920
ttcaaaactc cttccctgta tcgcaggtcg gtactgccac ggcggctaat aacttcttcc    1980
gccagattgg ttcggcattg ggtgcttcca tcgtgggttc gatgttcatt cacaatatgc    2040
agaatgagat ggctacccgt ttgcctgatg cccttgcatc gttgggcaag gaaggcgccg    2100
ctatttcgca gcagttccaa ggtgcagatg ccgccaactc cttgactccg cacgcagtcg    2160
cagagcttcc cgatgtcctc cgtgacgcta tcttaaattc ctacaatgac ggtctgaccc    2220
ccgtgattgg catgatggtg ccactggcca ttgttgcaat gctgattttg ttcccactgc    2280
gccaagagcg cttgaaggaa accatcgaat aa    2312

<210> SEQ ID NO 4
<211> LENGTH: 669
<212> TYPE: DNA
<213> ORGANISM: Unknown
<220> FEATURE:
<223> OTHER INFORMATION: ImpE1

<400> SEQUENCE: 4
ttgcatgctg tgcaagaagt taatgacaat gaagaagact ccctccctgg cagtgacctc    60
gggttaaggg agcagaagcg attggcaacc aagcatcgca tcgaagacgc cgcgacacgg    120
ttggttgatg aatcgagctt tgacaaagta acaattgaag aaatttgcga agccgccggg    180
atttcccgac gcaccttttt taattattc agcacgaaag aaagcgccgt tattggcgcg    240
tcctcggaac cgttgacgga aaagcaacgc aatgacttct gaatgctga cgccagcaat    300 ctcctgcagc tgatggttga gcagatcaaa caacacttgg agtcttctca ccagagtcaa    360
gcgattcacg accgtcgtca gcgaatcttt gcggatccgg atgtcgcggt acgtgcaatg    420
gcgtttcgca aggaacgctc acgggaaacc atggagctaa tcgctcaacg tcttcgggag    480
catcctgaag aacaacgcgc cccagaattg gatccggaaa cagaggcgat gctgctgagc    540
ggattcattc gcgaagccac ctggatggct atctcacgac ccgatcgtga ttgtgcactg    600
ccagtgggtg accgcatcta tcgcgcgatg gaattggtaa agaattacac gaaaggactg    660
gaatggtag    669

<210> SEQ ID NO 5
<211> LENGTH: 1650
<212> TYPE: DNA
<213> ORGANISM: Unknown
<220> FEATURE:
<223> OTHER INFORMATION: ImpE2

<400> SEQUENCE: 5
atggtagcta aaaactccac cccaagcacg gccggccacg ccagtgctca cactgcggaa    60
gaattcccag tggccaatgc tgaaatggca acgccttcag caatcgaccc aaaccacggt    120
aaaaagaccg cggataacgt cggcattatc ttcgctgcct tgatgctcac catgctgatg    180
```

```
agctctttgg ggcagatgat tttcggttcc gctctgccaa ccatcgtcgg cgagctcggc    240
ggcgtggacc agatgagctg ggtaatttca gcatttatgg tcaccatgac cattgctatg    300
ccactagccg gtcagctcgg tgaccgcatg ggccgcaagt gggtctacat ctcaggtatc    360
tccattttcg ttattggctc gacgtcggt ggctttgcca atggcatggg catgctgatc     420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt    720
gcggccatcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt gggtctggc catgatgggc    960 gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacggcg   1140
tttgctttgt ggtggatgtc ccagatgacc gttgagactt cattgaccgg tatcggagtt   1200
cgcttccttg tattcggtgt cggcttgggc tttgtcatgc aggtactggt gctgattgtt   1260
caaaactcct tccctgtatc gcaggtcggt actgccacgg cggctaataa cttcttccgc   1320
cagattggtt cggcattggg tgcttccatc gtgggttcga tgttcattca caatatgcag   1380
aatgagatgg ctaccgtttt gcctgatgcc cttgcatcgt tgggcaagga aggcgccgct   1440
atttcgcagc agttccaagg tgcagatgcc gccaactcct tgactccgca cgcagtcgca   1500
gagcttcccg atgtcctccg tgacgctatc ttaaattcct acaatgacgg tctgaccccc   1560
gtgattggca tgatggtgcc actggccatt gttgcaatgc tgattttgtt cccactgcgc   1620
caagagcgct tgaaggaaac catcgaataa                                     1650
```

<210> SEQ ID NO 6
<211> LENGTH: 29
<212> TYPE: DNA
<213> ORGANISM: Artificial Sequence
<220> FEATURE:
<223> OTHER INFORMATION: Primer impE1 kop-1

<400> SEQUENCE: 6

```
gctctagacg agaaagctaa agccggtga                                       29
```

<210> SEQ ID NO 7
<211> LENGTH: 36
<212> TYPE: DNA
<213> ORGANISM: Artificial Sequence
<220> FEATURE:
<223> OTHER INFORMATION: Primer impE1 kop-2

<400> SEQUENCE: 7

```
gtttttagct accattgtta caccccgtgc aagttt                               36
```

<210> SEQ ID NO 8
<211> LENGTH: 36
<212> TYPE: DNA
<213> ORGANISM: Artificial Sequence
<220> FEATURE:
<223> OTHER INFORMATION: Primer impE1 kop-3

<400> SEQUENCE: 8
gcacggggtg taacaatggt agctaaaaac tccacc       36

<210> SEQ ID NO 9
<211> LENGTH: 29
<212> TYPE: DNA
<213> ORGANISM: Artificial Sequence
<220> FEATURE:
<223> OTHER INFORMATION: Primer impE1 kop-4

<400> SEQUENCE: 9
gctctagaaa tagttgggga agtccactc       29

<210> SEQ ID NO 10
<211> LENGTH: 29
<212> TYPE: DNA
<213> ORGANISM: Artificial Sequence
<220> FEATURE:
<223> OTHER INFORMATION: Primer impE2 kop-1

<400> SEQUENCE: 10
gctctagact tggatgacct ggtggaaaa       29

<210> SEQ ID NO 11
<211> LENGTH: 36
<212> TYPE: DNA
<213> ORGANISM: Artificial Sequence
<220> FEATURE:
<223> OTHER INFORMATION: Primer impE2 kop-2

<400> SEQUENCE: 11
cttggagaaa atttcctacc attccagtcc tttcgt       36

<210> SEQ ID NO 12
<211> LENGTH: 36
<212> TYPE: DNA
<213> ORGANISM: Artificial Sequence
<220> FEATURE:
<223> OTHER INFORMATION: Primer impE2 kop-3

<400> SEQUENCE: 12
ggactggaat ggtaggaaat tttctccaag ggaaat       36

<210> SEQ ID NO 13
<211> LENGTH: 29
<212> TYPE: DNA
<213> ORGANISM: Artificial Sequence
<220> FEATURE:
<223> OTHER INFORMATION: Primer impE2 kop-4

<400> SEQUENCE: 13
ggactagtgg attgtgttga cgcacgatg       29

<210> SEQ ID NO 14
<211> LENGTH: 36
<212> TYPE: DNA
<213> ORGANISM: Artificial Sequence
<220> FEATURE:
<223> OTHER INFORMATION: Primer impE1E2 kop-2

<400> SEQUENCE: 14
cttggagaaa atttctgtta caccccgtgc aagttt       36

<210> SEQ ID NO 15
<211> LENGTH: 36
<212> TYPE: DNA
<213> ORGANISM: Artificial Sequence
<220> FEATURE:
<223> OTHER INFORMATION: Primer impE1E2 kop-3

<400> SEQUENCE: 15
gcacggggtg taacagaaat tttctccaag ggaaat                                    36

<210> SEQ ID NO 16
<211> LENGTH: 29
<212> TYPE: DNA
<213> ORGANISM: Artificial Sequence
<220> FEATURE:
<223> OTHER INFORMATION: Primer impE1 2-1

<400> SEQUENCE: 16
gctctagaga acggagtcat ctcctttgc                                            29

<210> SEQ ID NO 17
<211> LENGTH: 41
<212> TYPE: DNA
<213> ORGANISM: Artificial Sequence
<220> FEATURE:
<223> OTHER INFORMATION: Primer impE1 2-2

<400> SEQUENCE: 17
gggtctagag aagcggccgc ctaccattcc agtcctttcg t                              41

<210> SEQ ID NO 18
<211> LENGTH: 39
<212> TYPE: DNA
<213> ORGANISM: Artificial Sequence
<220> FEATURE:
<223> OTHER INFORMATION: Primer impE1 2-3

<400> SEQUENCE: 18
aaggaaaaaa gcggccgcga acggagtcat ctcctttgc                                 39

<210> SEQ ID NO 19
<211> LENGTH: 39
<212> TYPE: DNA
<213> ORGANISM: Artificial Sequence
<220> FEATURE:
<223> OTHER INFORMATION: Primer impE1 2-4

<400> SEQUENCE: 19
aaggaaaaaa gcggccgcct accattccag tcctttcgt                                 39

<210> SEQ ID NO 20
<211> LENGTH: 42
<212> TYPE: DNA
<213> ORGANISM: Artificial Sequence
<220> FEATURE:
<223> OTHER INFORMATION: Primer impE1E2 2-2

<400> SEQUENCE: 20
gggtctagag aagcggccgc ccaaacgctc tgcaagaaac tg                             42

<210> SEQ ID NO 21
<211> LENGTH: 38
<212> TYPE: DNA
<213> ORGANISM: Artificial Sequence
<220> FEATURE:
<223> OTHER INFORMATION: Primer impE1E2 2-4

```
<400> SEQUENCE: 21
ataagaatgc ggccgcccaa acgctctgca agaaactg                           38

<210> SEQ ID NO 22
<211> LENGTH: 29
<212> TYPE: DNA
<213> ORGANISM: Artificial Sequence
<220> FEATURE:
<223> OTHER INFORMATION: Primer impE1 Pcj7-1

<400> SEQUENCE: 22
gctctagagg tgagcgcgaa ggggacgcg                                     29

<210> SEQ ID NO 23
<211> LENGTH: 34
<212> TYPE: DNA
<213> ORGANISM: Artificial Sequence
<220> FEATURE:
<223> OTHER INFORMATION: Primer impE1 Pcj7-2

<400> SEQUENCE: 23
ggaattccat atgtgttaca ccccgtgcaa gttt                               34

<210> SEQ ID NO 24
<211> LENGTH: 31
<212> TYPE: DNA
<213> ORGANISM: Artificial Sequence
<220> FEATURE:
<223> OTHER INFORMATION: Primer impE1 Pcj7-3

<400> SEQUENCE: 24
ggaattccat atgcatgctg tgcaagaagt t                                  31

<210> SEQ ID NO 25
<211> LENGTH: 29
<212> TYPE: DNA
<213> ORGANISM: Artificial Sequence
<220> FEATURE:
<223> OTHER INFORMATION: Primer impE1 Pcj7-4

<400> SEQUENCE: 25
gctctagatt cagcattggc cactgggaa                                     29

<210> SEQ ID NO 26
<211> LENGTH: 29
<212> TYPE: DNA
<213> ORGANISM: Artificial Sequence
<220> FEATURE:
<223> OTHER INFORMATION: Primer impE2 Pcj7-1

<400> SEQUENCE: 26
gctctagatt gcatgctgtg caagaagtt                                     29

<210> SEQ ID NO 27
<211> LENGTH: 34
<212> TYPE: DNA
<213> ORGANISM: Artificial Sequence
<220> FEATURE:
<223> OTHER INFORMATION: Primer impE2 Pcj7-2

<400> SEQUENCE: 27
ggaattccat atgctaccat tccagtcctt tcgt                               34

<210> SEQ ID NO 28
```

```
<211> LENGTH: 31
<212> TYPE: DNA
<213> ORGANISM: Artificial Sequence
<220> FEATURE:
<223> OTHER INFORMATION: Primer impE2 Pcj7-3

<400> SEQUENCE: 28
ggaattccat atggtagcta aaaactccac c                                31

<210> SEQ ID NO 29
<211> LENGTH: 29
<212> TYPE: DNA
<213> ORGANISM: Artificial Sequence
<220> FEATURE:
<223> OTHER INFORMATION: Primer impE2 Pcj7-4

<400> SEQUENCE: 29
gctctagaaa tagttgggga agtccactc                                   29

<210> SEQ ID NO 30
<211> LENGTH: 32
<212> TYPE: DNA
<213> ORGANISM: Artificial Sequence
<220> FEATURE:
<223> OTHER INFORMATION: Primer Pcj7 F

<400> SEQUENCE: 30
ggaattccat atgtcccagc gctactaata gg                               32

<210> SEQ ID NO 31
<211> LENGTH: 33
<212> TYPE: DNA
<213> ORGANISM: Artificial Sequence
<220> FEATURE:
<223> OTHER INFORMATION: Primer Pcj7 R

<400> SEQUENCE: 31
ggaattccat atggagtgtt tcctttcgtt ggg                              33
```

IMP-PRODUCING MICROORGANISM AND METHOD OF PRODUCING IMP USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_441USPC_SEQUENCE_LISTING.txt. The text file is 17 KB, was created on Apr. 23, 2019, and is being submitted electronically via EFS-Web.

TECHNICAL FIELD

The present disclosure relates to a microorganism of the genus Corynebacterium producing 5'-inosine monophosphate, with an enhanced activity of an IMP export protein; a method for preparing 5'-inosine monophosphate using the same; a composition for producing 5'-inosine monophosphate; and a method for increasing export of 5'-inosine monophosphate.

BACKGROUND ART

5'-Inosine monophosphate (hereinafter referred to as 'IMP'), which is a nucleic acid-based material, is an intermediate in the nucleic acid metabolic pathway, and is used in various fields such as foods, medicines, and various medical applications. In particular, IMP is widely used as food seasoning additives or foods, together with 5'-guanine monophosphate (hereinafter referred to as 'GMP'). Although IMP itself is known to have a beef taste, it is also known to enhance the flavor of monosodium glutamate (MSG); therefore, IMP has drawn much attention as a savory nucleic acid-based seasoning.

Examples of methods for preparing IMP include a method of enzymatically degrading ribonucleic acid extracted from yeast cells (Japanese Patent Publication No. 1614/1957), a method of chemically phosphorylating inosine produced by fermentation (Agri. Biol. Chem., 36, 1511, etc.), and a method of culturing a microorganism which directly produces IMP and recovering the IMP in the culture medium. Among these methods, the most widely used is the method of using a microorganism capable of directly producing IMP.

DISCLOSURE

Technical Problem

In order to produce IMP in high yield using the method of directly producing IMP through microbial fermentation, the IMP should be smoothly exported. To accomplish such object, the present inventors conducted extensive research, and studied exporting proteins involved in the IMP exporting ability; as a result, they identified ImpE1 and ImpE2, which are proteins involved in export of IMP. It was confirmed that when the activities of ImpE1 and ImpE2, which are the proteins involved in the export of IMP, were enhanced, the IMP concentration was increased, thereby completing the present disclosure.

Technical Solution

An object of the present disclosure is to provide a microorganism of the genus Corynebacterium producing IMP, with an enhanced activity of an IMP export protein.

Another object of the present disclosure is to provide a method for preparing IMP, comprising culturing the microorganism of the genus Corynebacterium of the present disclosure in a medium.

Still another object of the present disclosure is to provide a composition for producing IMP, comprising a protein in which an activity of the IMP export protein of the present disclosure is enhanced.

Still another object of the present disclosure is to provide a method for increasing export of IMP, comprising enhancing an activity of the IMP export protein of the present disclosure in the microorganism of the genus Corynebacterium.

Advantageous Effects

In the present disclosure, IMP may be prepared using a microorganism of the genus Corynebacterium producing IMP, with an enhanced activity of an IMP export protein.

BEST MODE FOR CARRYING OUT THE INVENTION

Hereinbelow, the present disclosure will be described in detail. Meanwhile, each description and embodiment disclosed in the present disclosure may be applied to other descriptions and embodiments, respectively. That is, all combinations of various elements disclosed in the present disclosure fall within the scope of the present disclosure. Further, the specific descriptions disclosed below should not be construed as limiting the scope of the present disclosure.

In order to achieve the objects above, an aspect of the present disclosure is to provide a microorganism of the genus Corynebacterium producing IMP, with an enhanced activity of an IMP export protein.

As used herein, the term "5'-inosine monophosphate-exporting protein" refers to a protein involved in the extracellular export of 5'-inosine monophosphate (IMP). For the objects of the present disclosure, the term above may be used interchangeably with a protein having an IMP-exporting ability, a protein having a 5'-inosine monophosphate-exporting ability, an IMP export protein, etc., and specifically can be expressed as ImpE, more specifically, ImpE1 and ImpE2, but is not limited thereto. In addition, the protein may be derived from Corynebacterium sp., specifically, Corynebacterium stationis, but is not limited thereto. For example, a protein, which is derived from Corynebacterium stationis and which has an IMP-exporting ability and an effect corresponding thereto, can be used as the protein of the present disclosure.

The protein may be composed of, for example, an amino acid sequence of SEQ ID NO: 1 or 2, but includes sequences having the same activity as that of the protein, and those skilled in the art may obtain sequence information from GenBank of NCBI, a well-known database. In addition, the protein may include an amino acid sequence of SEQ ID NO: 1 or 2, or an amino acid sequence having at least 80%, 90%, 95%, 96%, 97%, 98%, or 99% homology or identity with SEQ ID NO: 1 or 2. In addition, it is apparent that a protein having a deletion, modification, substitution, or addition of some sequence may be used as the protein of the present disclosure as long as the amino acid sequence has the homology or identity above and exhibits an effect corresponding to that of the protein.

That is, although described as "a protein having an amino acid sequence of a particular SEQ ID NO" or "a protein consisting of an amino acid sequence of a particular SEQ ID NO" in the present disclosure, the protein may have an activity that is identical or corresponding to that of a protein consisting of an amino acid sequence of the corresponding SEQ ID NO. In such a case, it is obvious that any proteins having an amino acid sequence with deletion, modification, substitution, conservative substitution, or addition in part of the sequence also can be used in the present disclosure. For example, in the case of having the activity that is the same as or corresponding to that of the modified protein, it does not exclude an addition of a sequence upstream or downstream of the amino acid sequence, which does not alter the function of the protein, a mutation that may occur naturally, a silent mutation thereof, or a conservative constitution, and even when the sequence addition or mutation is present, it obviously belongs to the scope of the present disclosure.

As used herein, the term "homology" or "identity" refers to a degree of matching with two given amino acid sequences or nucleotide sequences, and may be expressed as a percentage.

The terms "homology" and "identity" may often be used interchangeably with each other.

The sequence homology or identity of conserved polynucleotide or polypeptide sequences may be determined by standard alignment algorithms and can be used with a default gap penalty established by the program being used. Substantially homologous or identical sequences are generally expected to hybridize under moderate or high stringency, along the entire length or at least about 50%, about 60%, about 70%, about 80%, or about 90% of the entire length of the sequences. Polynucleotides that contain degenerate codons instead of codons in the hybridizing polypeptides are also considered.

Whether any two polynucleotide or polypeptide sequences have a homology, similarity, or identity may be determined using a known computer algorithm such as the "FASTA" program (Pearson et al., (1988) [Proc. Natl. Acad. Sci. USA 85]: 2444: using default parameters in 2444). Alternately, it may be determined using the Needleman-Wunsch algorithm (Needleman and Wunsch, 1970, J. Mol. Biol. 48: 443-453), which is performed in the Needleman program of the EMBOSS package ((EMBOSS: The European Molecular Biology Open Software Suite, Rice et al., 2000, Trends Genet. 16: 276-277) (version 5.0.0 or versions thereafter) (GCG program package (Devereux, J., et al., Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1988) SIAM J Applied Math 48: 1073). For example, the homology, similarity, or identity may be determined using BLAST or ClustalW of the National Center for Biotechnology Information (NCBI).

The homology, similarity, or identity of polynucleotide or polypeptide sequences may be determined by comparing sequence information using, for example, the GAP computer program (e.g., Needleman et al., (1970), J Mol Biol. 48: 443) as published (e.g., Smith and Waterman, Adv. Appl. Math (1981) 2:482). In summary, the GAP program defines the homology, similarity, or identity as the value obtained by dividing the number of similarly aligned symbols (i.e., nucleotides or amino acids) into the total number of the symbols in the shorter of the two sequences. Default parameters for the GAP program may include (1) a unary comparison matrix (containing a value of 1 for identities and 0 for non-identities) and the weighted comparison matrix of Gribskov et al. (1986), *Nucl. Acids Res.* 14:6745, as disclosed in Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap (or a gap opening penalty of 10 and a gap extension penalty of 0.5); and (3) no penalty for end gaps. Accordingly, as used herein, the term "homology" or "identity" refers to relevance between sequences.

As used herein, the term "enhancement of activity" means that the activity of a protein is introduced, or that the activity is improved compared to an endogenous activity or an activity before modification of a microorganism. The "introduction" of the activity means that the activity of a specific protein, which is not naturally or artificially inherent to a microorganism, appears. The "endogenous activity" refers to the activity of a specific protein originally possessed by a parent strain before transformation when a microorganism is transformed by genetic variation caused by natural or artificially factors.

For example, the enhancement of activity may include both enhancing the activity by introducing a foreign IMP export protein into a host cell, or increasing the activity of an endogenous IMP export protein.

Specifically, in the present disclosure, the enhancement of activity may be conducted by the following methods:
1) increasing the copy number of a polynucleotide that codes for (that is, encodes) the protein;
2) modification of an expression regulatory sequence for increasing the polynucleotide expression;
3) modification of the polynucleotide sequence on a chromosome for enhancing an activity of the protein; or
4) a combination thereof, the methods not being limited thereto.

In method 1) above, the increase of the copy number of the polynucleotide encoding the enzymes may be achieved by operably linking the polynucleotide to the vector, or by inserting the same into the chromosome of the host cell, but is not particularly limited thereto. In addition, in one embodiment, the increase of the copy number may be performed by introducing an exogenous polynucleotide exhibiting the protein activity or a variant-form polynucleotide, in which a codon is optimized to the polynucleotide above, to the host cell. The exogenous polynucleotide may be used without limitation in its origin or sequence as long as it exhibits the same/similar protein activities. Those skilled in the art may carry out the introduction by appropriately selecting a known transformation method, and a protein may be produced by the expression of the introduced polynucleotide in the host cell to increase its activity. The increase in the copy number may be such that the polynucleotide is present in a tandem form continuously. In this case, polynucleotide sequences encoding different IMP export proteins may be present in a crossed, sequential, and repeating manner. When the polynucleotide is continuously present in the tandem form, an overlapping part may be occurred, but it is not limited thereto. Specifically, in the present disclosure, the copy number of the polynucleotide sequence of SEQ ID NO: 3, 4, or 5 may be increased.

In addition, 2) modification of an expression regulatory sequence for increasing the polynucleotide expression may be performed by inducing a modification on the expression regulatory sequence through deletion, insertion, non-conservative or conservative substitution of a nucleotide sequence, or a combination thereof; or by replacing the expression regulatory sequence with a nucleotide sequence having a stronger activity, but is not limited thereto. The expression regulatory sequence includes, but is not particularly limited to, a promoter, an operator sequence, a sequence coding for a ribosome-binding site, and a sequence regulating the termination of transcription and translation. Specifically, a strong heterologous promoter instead of the original promoter may be linked upstream of the polynucleotide expression unit, and examples of the strong promoter may include a CJ7 promoter, a lysCP1 promoter, an EF-Tu promoter, a groEL promoter, an aceA or aceB promoter, etc. The expression rate of the polynucleotide encoding the protein may be improved by operatively linking the promoter with the polynucleotide, but is not limited thereto.

Furthermore, 3) modification of a polynucleotide sequence on a chromosome, although not particularly limited thereto, may be performed by inducing a variation on the expression regulatory sequence through deletion, insertion, non-conservative or conservative substitution of a polynucleotide sequence, or a combination thereof in order to further enhance the activity of the polynucleotide sequence, or by replacing the sequence with a polynucleotide sequence which is modified to have stronger activity.

Lastly, 4) a modification method for enhancement by a combination of 1) to 3) may be carried out by applying one or more methods from among a method of increasing the copy number of a polynucleotide encoding the protein, a method of modifying the polynucleotide sequence for enhancing the polynucleotide expression, and a method of modifying the polynucleotide sequence on a chromosome and modifying an exogenous polynucleotide exhibiting the protein activity or a variant-form polynucleotide, in which a codon is optimized.

Additionally, it is apparent that a polynucleotide, which can be translated by the codon degeneracy into a protein consisting of the amino acid sequence of SEQ ID NO: 1 or 2, or into a protein having a homology thereto, also can be included. For example, the protein may be composed of a polynucleotide sequence of SEQ ID NO: 3, 4, or 5. In addition, a sequence, which encodes a protein having the activity of the protein consisting of an amino acid sequence of SEQ ID NO: 1 or 2 by hybridization under stringent conditions with a probe which can be prepared from known gene sequences, e.g., a complementary sequence to all or part of the nucleotide sequence, may be included without limitation. The term "stringent conditions" refers to conditions which permit a specific hybridization between polynucleotides. These conditions are specifically described in the literature (e.g., J. Sambrook et al., Sangdong). For example, the stringent conditions may include conditions in which genes having a high homology (e.g., 40% or more, specifically 90% or more, more specifically 95% or more, even more specifically 97% or more, and most specifically 99% or more) can hybridize between them, whereas genes having a lower homology thereof cannot hybridize with each other; or conditions for conventional southern hybridization (i.e., conditions for washing once, and specifically two or three times under a salt concentration and temperature corresponding to 60° C., 1×SSC, and 0.1% SDS; specifically under 60° C., 0.1×SSC, and 0.1% SDS; and more specifically under 68° C., 0.1×SSC, and 0.1% SDS).

Hybridization requires that two nucleic acids have complementary sequences, although mismatches between bases are possible depending on the severity of hybridization. The term "complementary" is used to describe the relationship between nucleotide bases capable of hybridizing with each other. For example, with respect to DNA, adenosine is complementary to thymine and cytosine is complementary to guanine. Therefore, the present disclosure may also include substantially similar nucleic acid sequences as well as isolated nucleic acid fragments complementary to the entire sequence.

Specifically, a polynucleotide having a homology can be detected using hybridization conditions including a hybridization step at a Tm value of 55° C. and using the conditions described above. Further, the Tm value may be 60° C., 63° C., or 65° C., but is not limited thereto; and can be suitably adjusted by those skilled in the art according to its object.

The appropriate stringency of hybridizing polynucleotides depends on the length and complementarity of the polynucleotides, and the variables are well known in the art (please refer to Sambrook et al., supra, 9.50-9.51, 11.7-11.8).

As used herein, the term "vector" refers to a DNA construct containing a nucleotide sequence of a polynucleotide encoding a desired protein, which is operably linked to a suitable regulatory sequence such that the desired protein is expressed in a suitable host cell. The regulatory sequence may include a promoter capable of initiating transcription, any operator sequence for regulating the transcription, a sequence encoding a suitable mRNA ribosome binding site, and a sequence regulating the termination of transcription and translation. After being transformed in a suitable host cell, the vector may be replicated or perform its function irrespective of the host genome, or may be integrated into the genome itself.

The vector used in the present disclosure is not particularly limited as long as it can be expressed in a host cell, and any vector known in the art can be used. Examples of a commonly used vector include a natural or recombinant plasmid, a cosmid, virus, and a bacteriophage. For example, pWE15, M13, MBL3, MBL4, LXII, ASHII, APII, t10, t11, Charon4A, and Charon21A may be used as a phage vector or a cosmid vector; and pBR-based, pUC-based, pBluescriptII-based, pGEM-based, pTZ-based, pCL-based, and pET-based may be used as a plasmid vector. Specifically, pDZ, pACYC177, pACYC184, pCL, pECCG117, pUC19, pBR322, pMW118, and pCC1BAC vectors may be used, but the vector is not limited thereto.

The vector that can be used in the present disclosure is not particularly limited, and a known expression vector may be used. In addition, a polynucleotide encoding a target protein may be inserted into a chromosome through a vector for intracellular chromosome insertion. The insertion of the polynucleotide into the chromosome may be performed by any methods, for example, by homologous recombination, but is not limited thereto. The vector may further include a selection marker for indicating the insertion of the vector into the chromosome. Adapted to indicate a cell transformed with the vector, that is, whether a target gene is inserted into the genome of the host cell, the selection marker may provide the cell with an ability to show drug resistance, cytotoxic agent resistance, auxotrophy, or selectable phenotype expression such as the expression of a surface protein. In the environment where a selective agent is treated, only the cells expressing the selection marker survive or express another phenotype, and thus transformed cells may be selected.

As used herein, the term "transformation" means that a vector containing a polynucleotide encoding a target protein is introduced into a host cell, such that a protein encoded by the polynucleotide is capable of being expressed in the host cell. The transformed polynucleotide may be any one regardless of the position as long as the polypeptide is capable of being expressed in the host cell, regardless of whether the polynucleotide is inserted and positioned into the chromosome of the host cell or positioned on an outer portion of the chromosome. In addition, the polynucleotide includes DNA and RNA, which encode a target protein. The polynucleotide may be introduced with any shape as long as the polynucleotide is capable of being introduced into the host cell to be expressed. For example, the polynucleotide may be introduced into the host cell as an expression cassette form, which is a gene structure including all factors required for self expression. The expression cassette may include a promoter, a transcription termination signal, a ribosome binding site, and a translation termination signal, that may be operably linked to the polynucleotide. The expression cassette may be an expression vector performing self-replication. In addition, the polynucleotide itself may be introduced into the host cell to be operably linked to the sequence required for expression in the host cell, but is not limited thereto. The transformation method includes any method of introducing a nucleic acid into a cell, and may be carried out by selecting a suitable standard technique known in the art. For example, examples of the method may include electroporation, calcium phosphate ($CaPO_4$), precipitation, calcium chloride ($CaCl_2$)) precipitation, microinjection, a polyethyleneglycol (PEG) technique, a DEAE-dextran technique, a cationic liposome technique, and a lithium acetate-DMSO technique, but are not limited thereto.

Additionally, the term "operably linked" refers to a functional connection between a promoter sequence, which initiates and mediates the transcription of the polynucleotide encoding the target protein of the present disclosure, and the polynucleotide sequence. Operable linking can be prepared using a gene recombination technique known in the art, and site-specific DNA cleavage and ligation can be performed using a restriction enzyme and ligase known in the art, but is not limited thereto.

As used herein, the term "microorganism of the genus *Corynebacterium* producing IMP" refers to a microorganism of the genus *Corynebacterium* having abilities to produce IMP through its native form or a variation. Specifically, in the present disclosure, the microorganism of the genus *Corynebacterium* producing IMP may be a microorganism which has improved abilities to produce IMP by inserting a gene related to the production mechanism of a native strain itself or exogenous IMP, or by enhancing or attenuating the activity of an endogenous gene. More specifically, the microorganism of the genus *Corynebacterium* producing IMP may be a microorganism in which abilities to produce IMP is improved compared to that of a parent strain before transformation or an unmodified microorganism.

In the present disclosure, "the microorganism of the genus *Corynebacterium*" may specifically be *Corynebacterium glutamicum, Corynebacterium ammoniagenes, Brevibacterium lactofermentum, Brevibacterium flavum, Corynebacterium thermoaminogenes, Corynebacterium efficiens, Corynebacterium stationis*, etc., but is not limited thereto. More specifically, in the present disclosure, the microorganism of the genus *Corynebacterium* may be *Corynebacterium stationis*. A specific example of the microorganism of the genus *Corynebacterium* may be *Corynebacterium stationis* in which abilities to produce IMP is improved by enhancing the activity of a protein having a function of exporting IMP to the outside of the cell, but is not limited thereto.

Another aspect of the present disclosure provides a method for preparing IMP, comprising culturing the microorganism of the genus *Corynebacterium* with an enhanced activity of the IMP export protein in a medium.

Specifically, the method of the present disclosure may further include a step of recovering IMP from the microorganism or medium.

In the method, culturing the microorganism may be carried out by batch culture, continuous culture, and fed-batch culture known in the art. Furthermore, as for the culture conditions, suitable pH (i.e., pH of 5 to 9, specifically pH 6 to 8, and most specifically pH 6.8) can be maintained using a basic chemical compound (i.e., sodium hydroxide, potassium hydroxide, or ammonia) or an acidic chemical compound (i.e., phosphoric acid or sulfuric acid). In addition, an aerobic condition can be maintained by introducing oxygen or an oxygen-containing gas mixture to a culture. The culture temperature may be maintained at 20° C. to 45° C., and specifically at 25° C. to 40° C. Further, the culture time may be about 10 to 160 hours. However, the culture conditions are not limited thereto. The IMP produced by the culture above may be excreted to a culture medium or may remain inside the cell.

Furthermore, the medium for culturing may comprise sugar and carbohydrate (e.g., glucose, sucrose, lactose, fructose, maltose, molasses, starch, and cellulose), oil and fat (e.g., soybean oil, sunflower seed oil, peanut oil, and coconut oil), fatty acid (e.g., palmitic acid, stearic acid, and linoleic acid), alcohol (e.g., glycerol and ethanol), and organic acid (e.g., acetic acid) individually or in combination as a carbon source, but the medium is not limited thereto. In addition, the medium for culturing may comprise a nitrogen-containing organic compound (e.g., peptone, yeast extract, meat juice, malt extract, corn solution, soybean meal powder, and urea), or an inorganic compound (e.g., ammonium sulfate, ammonium chloride, phosphate or ammonium, ammonium carbonate, and ammonium nitrate) individually or in combination as a nitrogen source, but the medium is not limited thereto. In addition, the medium for culturing may comprise potassium dihydrogen phosphate, dipotassium hydrogen phosphate, or a sodium-containing salt corresponding thereto individually or in combination as a phosphorous source, but the medium is not limited thereto. Additionally, the medium may comprise other essential growth-simulating substances including metal salts (e.g., magnesium sulfate or iron sulfate), amino acids, and vitamins.

The method of the present disclosure for recovering the IMP produced from the culturing method above may collect desired IMP from the culture medium using a suitable method known in the art according to the culturing method. For example, centrifugation, filtration, anion exchange chromatography, crystallization, HPLC, etc. may be used, and desired IMP can be recovered from a medium or a microorganism using a suitable method known in the art.

Additionally, the recovering method above may include a purification process, and may be carried out using a suitable method known in the art. Therefore, the recovered IMP may be in a purified form or a microbial fermented broth containing IMP.

Still another aspect of the present disclosure provides a composition for producing IMP, comprising the protein of the present disclosure, which consists of the amino acid sequence of SEQ ID NO: 1 or 2, or a polynucleotide encoding the same.

The composition of the present disclosure may further include, without limitation, a constitution capable of operating the polynucleotide. In addition, in the composition of the present disclosure, the polynucleotide may be in a form included within a vector so that a gene operably linked with the introduced host cell can be expressed.

Additionally, the composition may further include any suitable excipients conventionally used in the composition for producing IMP. Such excipients may be, for example, preservatives, humectants, suspending agents, buffers, stabilizing agents, or isotonic agents, but are not limited thereto.

Still another aspect of the present disclosure provides use of the protein consisting of the amino acid sequence of SEQ ID NO: 1 or 2 for increasing the production of IMP in the microorganism of the genus *Corynebacterium*.

Still another aspect of the present disclosure provides a method for increasing the export of IMP, comprising enhancing an activity of the protein consisting of the amino acid sequence of SEQ ID NO: 1 or 2 in the microorganism of the genus *Corynebacterium*.

Still another aspect of the present disclosure provides use of the protein consisting of the amino acid sequence of SEQ ID NO: 1 or 2 for increasing the export of IMP in the microorganism of the genus *Corynebacterium*.

The terms "protein consisting of the amino acid sequence of SEQ ID NO: 1 or 2", "enhancement", and "microorganism of the genus *Corynebacterium*" are as described above.

DETAILED DESCRIPTION OF THE EMBODIMENT

Hereinbelow, the present disclosure will be described in detail with accompanying exemplary embodiments. However, the exemplary embodiments disclosed herein are only for illustrative purposes and should not be construed as limiting the scope of the present disclosure.

Example 1: Production of Genomic DNA Library

A genomic DNA library of *Corynebacterium stationis* ATCC6872 was produced in order to identify the membrane protein of *Corynebacterium*, which is involved in the IMP export.

Thereafter, since the wild-type strain of the genus *Corynebacterium* cannot produce IMP or produces a very small amount of IMP, the strain CJI0323 derived from ATCC6872 having abilities to produce IMP was produced to confirm the abilities to produce IMP. The genomic DNA library of the ATCC6872 was transformed into the produced strain CJI0323, and then screening was carried out for the wild-type membrane protein involved in the IMP export. Specific experiments are as follows.

Example 1-1: Selection of IMP-Producing Strain, CJI0323

ATCC6872 ($10^7$ cells/mL to $10^8$ cells/mL) was suspended in a phosphate buffer (pH 7.0) or in a citrate buffer (pH 5.5) in order to prepare an ATCC6872-derived IMP-producing strain, and then mutation was induced by UV treatment. The resultants were washed twice with a 0.85% saline solution, and then diluted and smeared on a medium containing an appropriate concentration of a substance to be resistant to a minimal medium containing 1.7% agar. Thereafter, colonies were obtained. Each colony was cultured in a nutrient medium and cultured in a seed medium for 24 hours. After 3 to 4 days of culturing in a fermentation medium, colonies with the highest amount of IMP accumulated in the culture medium were selected. In order to produce a high-concentration IMP producing-strain, and to provide adenine auxotrophy, guanine leakage, lysozyme susceptibility, 3,4-dihydroproline resistance, streptomycin resistance, azetidine carboxylic acid resistance, thiaproline resistance, azaserine resistance, sulfaguanidine resistance, norvaline resistance, and trimethoprim resistance, the procedures above were performed sequentially for each substance. CJI0323, which is resistant to the substances above and has excellent abilities to produce IMP, was ultimately selected. Table 1 below shows the resistance of ATCC6872 compared to that of CJI0323.

TABLE 1

| Properties | ATCC6872 | CJI0323 |
|---|---|---|
| Adenine auxotrophy | Non-auxotrophy | Auxotrophy |
| Guanine leakage | Non-auxotrophy | Leaky auxotrophy |
| Lysozyme susceptibility | 80 µg/mL | 8 µg/mL |
| 3,4-Dihydroproline resistance | 1000 µg/mL | 3500 µg/mL |
| Streptomycin resistance | 500 µg/mL | 2000 µg/mL |
| Azetidine carboxylic acid resistance | 5 mg/mL | 30 mg/mL |
| Thiaproline resistance | 10 µg/mL | 100 µg/mL |
| Azaserine resistance | 25 µg/mL | 100 µg/mL |
| Sulfaguanidine resistance | 50 µg/mL | 200 µg/mL |
| Norvaline resistance | 0.2 mg/mL | 2 mg/mL |
| Trimethoprim resistance | 20 µg/mL | 100 µg/mL |

The compositions of the media are as follows:

Minimal medium: 2% glucose, 0.3% sodium sulfate, 0.1% $KH_2SO_4$, 0.3% $K_2HPO_4$, 0.3% magnesium sulfate, calcium chloride (10 mg/L), iron sulfate (10 mg/L), zinc sulfate (1 mg/L), manganese chloride (3.6 mg/L), L-cysteine (20 mg/L), calcium pantothenate (10 mg/L), thiamine hydrochloride (5 mg/L), biotin (30 µg/L), adenine (20 mg/L), guanine (20 mg/L), pH 7.3

Nutrient medium: 1% peptone, 1% meat juice, 0.25% sodium chloride, 1% yeast extract, 2% agar, pH 7.2

Seed medium: 1% glucose, 1% peptone, 1% meat juice, 1% yeast extract, 0.25% sodium chloride, adenine (100 mg/L), guanine (100 mg/L), pH 7.5

Fermentation medium: 0.1% sodium glutamate, 1% ammonium chloride, 1.2% magnesium sulfate, 0.01% calcium chloride, iron sulfate (20 mg/L), manganese sulfate (20 mg/L), zinc sulfate (20 mg/L), copper sulfate (5 mg/L), L-cysteine (23 mg/L), alanine (24 mg/L), nicotinic acid (8 mg/L), biotin (45 µg/L), thiamin hydrochloride (5 mg/L), adenine (30 mg/L), 1.9% phosphoric acid (85%), 2.55% glucose, 1.45% fructose

Example 1-2: Experiment of CJI0323 Fermentation Titer

The seed medium (2 mL) was dispensed into test tubes (18 mm diameter), which were then autoclaved and each inoculated with ATCC6872 and CJI0323. Thereafter, the resultants were shake-cultured at 30° C. for 24 hours, and then used as seed culture solutions. The fermentation medium (29 mL) was dispensed into Erlenmeyer flasks (250 mL) and autoclaved at 121° C. for 15 minutes. Thereafter, each seed culture solution (2 mL) was inoculated thereto, and then the resultants were cultured for 3 days. The culture conditions were set to 170 rpm, a temperature of 30° C., and a pH of 7.5.

After the culturing, the amount of IMP produced was measured using HPLC (SHIMAZDU LC20A), and the results of the culturing are shown in Table 2 below.

TABLE 2

| Strain | IMP (g/L) |
|---|---|
| ATCC6872 | 0 |
| CJI0323 | 9.52 |

Example 1-3: Finding of Exporting Protein

Screening conditions showing growth inhibition of the strain CJI0323 were established by additionally adding IMP in the minimal medium supplemented with 1.7% agar. ATCC6872, the genomic library plasmid, was transformed into the strain CJI0323 using electroporation (van der Rest et al. 1999). Colonies were selected in which the decrease in growth was released under the medium conditions supplemented with an excess of IMP. Plasmids were obtained from the selected colonies and analyzed by sequencing techniques. From the above, one kind of membrane protein involved in releasing the decrease of growth was identified under the condition of addition of excess IMP.

The one kind of the *Corynebacterium* membrane protein was identified by the amino acid sequence of SEQ ID NO: 2 and the nucleotide sequence of SEQ ID NO: 5 (NCBI GenBank: NZ_CP014279, WP_066795121, MFS transporter). The membrane protein is known as the MFS transporter, but its specific function has not been confirmed, and further, its function regarding the IMP export is still unknown. In the present disclosure, the membrane protein was named ImpE2(WT).

Example 2: Identification of ImpE1 and ImpE2

Example 2-1: Confirmation of impE1 and impE2

In order to examine the function of the membrane protein ImpE2, the gene structure of SEQ ID NO: 5 was identified in NCBI (NCBI GenBank: NZ_CP014279, WP_066795121, MFS transporter). It was confirmed that SEQ ID NO: 5 (impE2) was overlapped with the 7 bp starting portion of the ORF of a gene, which is located upstream of impE2 (NCBI GenBank: NZ_CP014279, WP_066795119, transcriptional regulator). The function of the protein encoded by the gene or the corresponding gene located upstream of impE2 has not been confirmed; in the present disclosure, such protein was named ImpE1(WT) (the amino acid sequence of SEQ ID NO: 1 and the nucleotide sequence of SEQ ID NO: 4).

Example 2-2: Preparation of impE1- or impE2-Deficient Vectors

In order to determine whether the IMP exporting ability is reduced when ImpE1 or ImpE2, which is involved in releasing the decrease of growth by IMP and which was identified through Examples 1 and 2-1, was deleted, preparation of deficient vectors was attempted for each gene.

The gene fragments for constructing the vectors were obtained by PCR using ATCC6872, the genomic DNA, as a template.

Specifically, primers of SEQ ID NOS: 6 and 7 and primers of SEQ ID NOS: 8 and 9 were used for PCR for impE1; and primers of SEQ ID NOS: 10 and 11 and primers of SEQ ID NOS: 12 and 13 were used for PCR for impE2 (Table 3).

TABLE 3

| SEQ ID NO: | Primer | Sequence (5' to 3') |
|---|---|---|
| 6 | impE1 kop-1 | GCTCTAGACGAGAAAGCTAAAGCCGGTGA |
| 7 | impE1 kop-2 | GTTTTTAGCTACCATTGTTACACCCCGTG CAAGTTT |

TABLE 3-continued

| SEQ ID NO: | Primer | Sequence (5' to 3') |
|---|---|---|
| 8 | impE1 kop-3 | GCACGGGGTGTAACAATGGTAGCTAAAAA CTCCACC |
| 9 | impE1 kop-4 | GCTCTAGAAATAGTTGGGGAAGTCCACTC |
| 10 | impE2 kop-1 | GCTCTAGACTTGGATGACCTGGTGGAAAA |
| 11 | impE2 kop-2 | CTTGGAGAAAATTTCCTACCATTCCAGTC CTTTCGT |
| 12 | impE2 kop-3 | GGACTGGAATGGTAGGAAATTTTCTCCAA GGGAAAT |
| 13 | impE2 kop-4 | GGACTAGTGGATTGTGTTGACGCACGATG |
| 14 | impE1E2 kop-2 | CTTGGAGAAAATTTCTGTTACACCCCGTG CAAGTTT |
| 15 | impE1E2 kop-3 | GCACGGGGTGTAACAGAAATTTTCTCCAA GGGAAAT |

The primers used were produced based on information on the *Corynebacterium stationis* (ATCC6872) gene (NCBI Genbank: NZ_CP014279) registered in the NIH GenBank and the nucleotide sequences adjacent thereto.

PCR was conducted with denaturation at 94° C. for 5 minutes, followed by repeating the cycle 25 times including denaturation at 94° C. for 30 seconds, annealing at 52° C. for 3 minutes, and polymerization at 72° C. for 1 minute, and then polymerization at 72° C. for 5 minutes. Overlapping polymerase chain reaction was performed using two fragments of the gene impE1, which was enhanced using the primers of SEQ ID NOS: 6 and 7 and the primers of SEQ ID NOS: 8 and 9, as a template. As a result, a polynucleotide template (1.8 kbp) was obtained. The obtained gene fragment was digested with a restriction enzyme, XbaI. pDZ-ΔimpE1 was prepared using the pDZ vector (Korean Patent No. 10-0924065 and International Patent Publication No. 2008-033001), which was obtained by digesting the gene fragment with the restriction enzyme, XbaI, using T4 ligase. In addition, overlapping polymerase chain reaction was conducted using a fragment of the gene impE2 enhanced by the primers of SEQ ID NOS: 10 and 11 and two fragments of the gene impE2 enhanced by the primers of SEQ ID NOS: 12 and 13 as templates, and a polynucleotide template (1.7 kbp) was obtained. The obtained gene fragments were digested with restriction enzymes, XbaI and speI. The gene fragments were cloned using T4 ligase into the pDZ vector, which was digested with the restriction enzyme, XbaI, and then pDZ-ΔimpE2 was prepared.

Example 2-3: Preparation of impE1- and impE2-Deficient Vectors

Since the genes impE1 and impE2, which encode proteins involved in releasing the decrease of growth by IMP, are overlapped, there is a need to regulate both genes simultaneously. Therefore, attempts were made to prepare a vector in which both impE1 and impE2 are deficient.

For PCR of impE1 and impE2, primers of SEQ ID NOS: 6 and 14 and primers of SEQ ID NOS: 15 and 13 were used. The primers used were produced based on information on the *Corynebacterium stationis* (ATCC6872) gene (NCBI Genbank: NZ_CP014279) registered in the NIH GenBank and the nucleotide sequences adjacent thereto. Overlapping polymerase chain reaction was conducted using a fragment of the gene impE1 enhanced by the primers of SEQ ID NOS: 6 and 14 and two fragments of the gene impE2 enhanced by the primers of SEQ ID NOS: 15 and 13 as templates, and a polynucleotide template (2.0 kbp) was obtained. The obtained gene fragments were digested with XbaI and speI, respectively. The gene fragments were cloned using T4 ligase into the pDZ vector, which was digested with the restriction enzyme, XbaI, and then, pDZ-ΔimpE1E2 was prepared.

Example 2-4: Preparation of impE1- and impE2-deficient strains

The two plasmids prepared in Example 2-2 and the one plasmid prepared in Example 2-3 were each transformed into CJI0323 by electroporation (using the transformation method disclosed in Appl. Microbiol. Biotechnol. (1999) 52:541-545). The strains in which the vector was inserted on the chromosome by recombination of the homologous sequences were selected on a medium containing kanamycin (25 mg/L). The selected primary strains were subjected to a second cross-over. The gene defect in the finally transformed strains was determined by carrying out PCR using primer pairs of SEQ ID NOS: 6 and 9, SEQ ID NOS: 10 and 13, and SEQ ID NOS: 6 and 13.

The selected strains were named CJI0323_ΔimpE1, CJI0323_ΔimpE2, and CJI0323_ΔimpE1E2. In addition, the abilities to produce IMP of the strains above was evaluated.

The seed medium (2 mL) was dispensed into test tubes (18 mm diameter), which were then autoclaved and each inoculated with CJI0323, CJI0323_ΔimpE1, CJI0323_ΔimpE2, and CJI0323_ΔimpE1E2. Thereafter, the resultants were shake-cultured at 30° C. for 24 hours, and then used as seed culture solutions. The fermentation medium (29 mL) was dispensed into Erlenmeyer flasks (250 mL) used for shaking and autoclaved at 121° C. for 15 minutes. Thereafter, each seed culture solution (2 mL) was inoculated thereto, and the resultants were cultured for 3 days. The culture conditions were set to 170 rpm, a temperature of 30° C., and a pH of 7.5.

After completion of the culture, the amount of IMP produced was measured by HPLC, and the results of the culture are shown in Table 4 below.

TABLE 4

| Strain | IMP (g/L) |
|---|---|
| CJI0323 | 9.52 |
| CJI0323_ΔimpE1 | 1.92 |
| CJI0323_ΔimpE2 | 1.88 |
| CJI0323_ΔimpE1E2 | 1.80 |

The accumulated IMP amount in each strain was compared with that of the parent strain, *Corynebacterium stationis* CJI0323. As a result, it was found that, as shown in Table 4 above, the IMP concentrations of the strains, CJI0323_ΔimpE1, CJI0323_ΔimpE2, and CJI0323_ΔimpE1E2, were reduced by about 8 g/L under the same conditions compared to the parent strain, confirming that ImpE1 and ImpE2 are proteins involved in the IMP export.

Example 3: Enhancement of Wild-Type impE1 and impE2

The wild-type strain of the genus *Corynebacterium* cannot produce IMP or produces a very small amount of IMP. Therefore, in 010323, which is the strain producing IMP, the protein ImpE was knocked out and then restored by introducing the wild-type protein, ImpE, and further, the activity of ImpE was enhanced; thereby confirming that the ability of exporting IMP was increased by the enhancement of the wild-type ImpE. The enhancement of the protein activity was achieved by using a method of "increasing the copy number" and a method of enhancing a promoter, among enhancement methods.

Example 3-1: Preparation Wild-Type impE1- and impE2-Introduced Vector

In order to prepare the strain in which wild-type ImpE is introduced, the gene fragments for preparing the vector were obtained through PCR using ATCC6872 genomic DNA as a template. For PCR of wild-type impE1 and impE2, primers of SEQ ID NOS: 6 and 13 were used. The entire fragments of the wild-type impE1-impE2 gene, which was enhanced by the primers of SEQ ID NOS: 6 and 13, were treated with the restriction enzymes, XbaI and SpeI, and then cloned into the XbaI restriction enzyme site of the pDZ vector to prepare pDZ-impE1E2(WT).

Example 3-2: Preparation of Wild-Type impE1-Enhanced Vector

In order to produce the impE1-enhanced vector, the gene fragments for preparing the vector were obtained by PCR using ATCC6872 genomic DNA as a template. In order to enhance impE1, primers of SEQ ID NOS: 16 and 17 including about 370 bp of impE1 upstream, which is considered to be a promoter region, were used for enhancement. The enhanced impE1 gene fragments were treated with the restriction enzyme, XbaI, and then cloned into the XbaI restriction enzyme site of the pDZ vector to prepare pDZ-impE1(WT)2-1. Thereafter, for preparing two copies of the vector, impE1 was subjected to PCR with a pair of primers of SEQ ID NOS: 18 and 19. Each obtained DNA fragment was digested with NotI, which is a DNA restriction enzyme, and cloned into pDZ-impE1(WT)2-1 digested with the same DNA restriction enzyme. The prepared vector was named pDZ-impE1(WT) 2X.

Example 3-3: Preparation of Wild-Type impE1- and impE2-Enhanced Vector

In order to prepare the strain in which both impE1 and impE2 were enhanced, the integrating genes of wild-type impE1 and impE2 were enhanced by PCR using primers of SEQ ID NOS: 16 and 20. The enhanced gene fragments were treated with XbaI, a restriction enzyme, and then cloned into the XbaI restriction enzyme site of the pDZ vector to prepare pDZ-impE1E2(WT)2-1. Thereafter, for preparing two copies of the vector, impE1E2 was subjected to PCR with a pair of primers of SEQ ID NOS: 18 and 21. Each obtained DNA fragment was digested with NotI, which is a DNA restriction enzyme, and cloned into pDZ-impE1E2 (WT)2-1 digested with the same DNA restriction enzyme. The prepared vector was named pDZ-impE1E2(WT) 2X.

TABLE 5

| SEQ ID NO: | Primer | Sequence (5' to 3') |
|---|---|---|
| 16 | impE1 2-1 | GCTCTAGAGAACGGAGTCATCTCCTTTGC |
| 17 | impE1 2-2 | GGGTCTAGAGAAGCGGCCGCCTACCATTCCAGTCCTTTCGT |
| 18 | impE1 2-3 | AAGGAAAAAAGCGGCCGCGAACGGAGTCATCTCCTTTGC |
| 19 | impE1 2-4 | AAGGAAAAAAGCGGCCGCCTACCATTCCAGTCCTTTCGT |
| 20 | impE1E2 2-2 | GGGTCTAGAGAAGCGGCCGCCCAAACGCTCTGCAAGAAACTG |
| 21 | impE1E2 2-4 | ATAAGAATGCGGCCGCCCAAACGCTCTGCAAGAAACTG |

Example 3-4: Evaluation of Wild-Type impE1- and impE2-Introduced/Enhanced Strains pDZ-impE1E2(WT), prepared in Example 3-1, was transformed into CJI0323_ΔimpE1E2, the strain prepared in Example 2, by electroporation (using the transformation method disclosed in Appl. Microbiol. Biotechnol. (1999) 52:541-545). Thereafter, the strains in which the vector was inserted on the chromosome by recombination of the homologous sequences were selected on a medium containing kanamycin (25 mg/L). The selected primary strains were subjected to a second cross-over. The gene introduction in the finally transformed strains was determined by carrying out PCR using primer pairs of SEQ ID NOS: 6 and 13. Thereafter, the prepared strain, CJI0323_ΔimpE1_E2_impE1E2(WT), was evaluated to determine the abilities to produce IMP when wild-type impE1 and impE2 were introduced into the strain, CJI0323.

Additionally, the vectors pDZ-impE1(WT) 2X and pDZ-impE1E2(WT) 2X were transformed into the strain CJI0323_ΔimpE1_E2_impE1E2(WT) using electroporation, and then the strains in which the vector was inserted on the chromosome by recombination of the homologous sequences were selected on a medium containing kanamycin (25 mg/L). The selected primary strains were subjected to a second cross-over. The gene enhancement in the finally transformed strains was determined by carrying out PCR using primer pairs of SEQ ID NOS: 16 and 19 and SEQ ID NOS: 16 and 21. CJI0323_ΔimpE1E2_impE1E2(WT), CJI0323_ΔimpE1E2_impE1E2(WT)_impE1(WT) 2X, and CJI0323_ΔimpE1E2_impE1E2(WT)_impE1E2(WT) 2X were cultured in the same manner as in Example 2-4 to obtain strains, and the abilities to produce IMP of the strains above was evaluated. After completion of the culture, the amount of IMP produced was measured by HPLC, and the results of the culture are shown in Table 6 below.

TABLE 6

| Strain | IMP (g/L) |
|---|---|
| CJI0323_ΔimpE1E2 | 1.80 |
| CJI0323_ΔimpE1E2_impE1E2(WT) | 2.32 |
| CJI0323_ΔimpE1E2_impE1E2(WT)_impE1(WT) 2X | 2.52 |
| CJI0323_ΔimpE1E2_impE1E2(WT)_impE1E2(WT) 2X | 2.97 |

The accumulated IMP amount in each strain was compared with that of the parent strain, Corynebacterium stationis CJI0323_ΔimpE1E2_impE1E2(WT). As a result, it was found that, as shown in Table 6 above, the IMP concentration of the strain, in which the activities of ImpE1 or ImpE1 and ImpE2 were simultaneously enhanced under the same conditions, was increased by up to 28%. For a microorganism of the genus Corynebacterium, which does not produce IMP or produces a trace amount thereof, the increase in the IMP production due to the increase of the activity of the protein, ImpE, can be interpreted as very meaningful.

The prepared strains CJI0323 and CJI0323_ΔimpE1E2_impE1E2(WT)_impE1E2(WT) 2X(CJI2236) were named as Corynebacterium stationis CN01-0323 and Corynebacterium stationis CN01-2236, respectively. The strains were deposited under the Budapest Treaty to the Korean Culture Center of Microorganisms (KCCM) on Nov. 7, 2017, and Oct. 25, 2017, respectively. In addition, the strains were designated as KCCM12151P and KCCM12137P, respectively.

Example 3-5: Preparation of Enhanced Promoter-Enhanced Vector of Wild-Type impE1 or impE2

The gene fragments for preparing the vector that replaces the promoter of each gene with an enhanced promoter were obtained by PCR using ATCC6872 genomic DNA as a template.

For the enhanced promoter, a Pcj7 promoter (Korean Laid-open Patent Publication No. 10-0620092), which is reported to be strongly expressed in Corynebacterium stationis, was used.

For PCR of impE1, each gene fragment enhanced using primers of SEQ ID NOS: 22 and 13 and primers of SEQ ID NOS: 24 and 25 was treated with restriction enzymes, XbaI and NdeI, and then cloned into the XbaI restriction enzyme site of the pDZ vector. In order to enhance the Pcj7 gene fragments, fragments obtained by performing PCR with primers of SEQ ID NOS: 30 and 31 using ATCC6872 genomic DNA as a template were treated with NdeI, and the prepared vector was treated with NdeI to prepare the vector, pDZ-Pcj7_impE1(WT).

For PCR of impE2, each gene fragment enhanced using primers of SEQ ID NOS: 26 and 27 and primers of SEQ ID NOS: 28 and 29 was treated with restriction enzymes, XbaI and NdeI, and then cloned into the XbaI restriction enzyme site of the pDZ vector. The obtained Pcj7 gene fragments and the prepared vector were treated with NdeI to prepare the vector, pDZ-Pcj7_impE2(WT).

TABLE 7

| SEQ ID NO: | Primer | Sequence (5' to 3') |
|---|---|---|
| 22 | impE1 Pcj7-1 | GCTCTAGAGGTGAGCGCGAAGGGGACGCG |
| 23 | impE1 Pcj7-2 | GGAATTCCATATGTGTTACACCCCGTGCAAGTTT |
| 24 | impE1 Pcj7-3 | GGAATTCCATATGCATGCTGTGCAAGAAGTT |
| 25 | impE1 Pcj7-4 | GCTCTAGATTCAGCATTGGCCACTGGGAA |
| 26 | impE2 Pcj7-1 | GCTCTAGATTGCATGCTGTGCAAGAAGTT |
| 27 | impE2 Pcj7-2 | GGAATTCCATATGCTACCATTCCAGTCCTTTCGT |

TABLE 7-continued

| SEQ ID NO: | Primer | Sequence (5' to 3') |
|---|---|---|
| 28 | impE2 Pcj7-3 | GGAATTCCATATGGTAGCTAAAAACTCCACC |
| 29 | impE2 Pcj7-4 | GCTCTAGAAATAGTTGGGGAAGTCCACTC |
| 30 | Pcj7 F | GGAATTCCATATGTCCCAGCGCTACTAATAGG |
| 31 | Pcj7 R | GGAATTCCATATGGAGTGTTTCCTTTCGTTGGG |

Example 3-6: Evaluation of Strain in which Wild-Type impE1 and impE2 Promoters are Replaced Each of the two plasmids prepared in Example 4-1 was transformed into CJI0323_ΔimpE1_E2_impE1E2(WT), the strain prepared in Example 3-3, by electroporation (using the transformation method disclosed in Appl. Microbiol. Biotechnol. (1999) 52:541-545). Thereafter, the strains in which the vector was inserted on the chromosome by recombination of the homologous sequences were selected on a medium containing kanamycin (25 mg/L). The selected primary strains were subjected to a second cross-over. The gene enhancement in the finally transformed strains was determined by carrying out PCR using primer pairs of SEQ ID NOS: 22 and 25 and SEQ ID NOS: 26 and 27. The two strains prepared above were named CJI0323_ΔimpE1E2_impE1E2(WT)_Pcj7/impE1(WT) and CJI0323_ΔimpE1E2_impE1E2(WT)_Pcj7/impE2(WT). Additionally, based on the prepared strain, CJI0323_ΔimpE1E2_impE1E2(WT)_Pcj7/impE1(WT), pDZ-Pcj7_impE2(WT) was transformed. Thereafter, the strain in which the vector was inserted on the chromosome by recombination of homologous sequences was selected on a medium containing kanamycin (25 mg/L). The selected primary strain was subjected to a second cross-over. The gene enhancement in the finally transformed strain was determined by carrying out PCR using primer pairs of SEQ ID NOS: 26 and 29. The strain prepared above was named CJI0323_ΔimpE1E2_impE1E2(WT)_Pcj7/impE1(WT)_Pcj7/impE2(WT). Thereafter, each of the prepared strains, CJI0323_ΔimpE1E2_impE1E2(WT)_Pcj7/impE1(WT), CJI0323_ΔimpE1E2_impE1E2(WT)_Pcj7/impE2(WT), and CJI0323_ΔimpE1E2_impE1E2(WT)_Pcj7/impE1(WT)_Pcj7/impE2(WT), was cultured in the same manner as in Example 2-4, and then the IMP productivities thereof were evaluated.

After completion of the culture, the amount of IMP produced was measured by HPLC, and the results of the culture are shown in Table 8 below.

TABLE 8

| Strain | IMP (g/L) |
|---|---|
| CJI0323_ΔimpE1E2_impE1E2(WT) | 2.32 |
| CJI0323_ΔimpE1E2_impE1E2(WT)_Pcj7/impE1(WT) | 2.47 |
| CJI0323_ΔimpE1E2_impE1E2(WT)_Pcj7/impE2(WT) | 2.81 |
| CJI0323_ΔimpE1E2_impE1E2(WT)_Pcj7/impE1(WT)_Pcj7/impE2(WT) | 2.97 |

The accumulated IMP amount in each strain was compared with that of the parent strain, *Corynebacterium stationis* CJI0323_ΔimpE1E2_impE1E2(WT). As a result, it was found that, as shown in Table 8 above, the IMP concentrations of the strains, in which the activities of ImpE1 and/or ImpE2 were enhanced, were increased by up to 28% under the same conditions.

The prepared strains CJI0323_ΔimpE1E2_impE1E2(WT)_Pcj7/impE1(WT) and CJI0323_ΔimpE1E2_impE1E2(WT)_Pcj7/impE2(WT) were deposited under the Budapest Treaty to the Korean Culture Center of Microorganisms (KCCM) on Nov. 2, 2018. In addition, the strains were designated as KCCM12357P and KCCM12358P, respectively.

Example 4: Enhancement of IMP-Producing Strain-Based impE1 and impE2

Example 4-1: Preparation of IMP-Producing Strain-Based impE1 and impE2

In order to confirm the enhancement effects of impE1 and impE2, An IMP-producing strains were prepared in which the activities of adenylosuccinate synthetase and IMP dehydrogenase, which correspond to the IMP degradation pathway in ATCC6872, were attenuated. The initiation codon was changed by changing the first base from 'a' to 't' in each nucleotide sequence of the genes purA and guaB encoding the above two enzymes. The strain in which the expressions of the two genes were attenuated in ATCC6872 was named CJI9088. The vectors pDZ-impE1(WT) 2X and pDZ-impE1E2(WT)2X, prepared in Example 3-3, were transformed into the strain CJI9088 by electroporation, and the strains in which the vectors were inserted on the chromosome by recombination of the homologous sequences were selected on a medium containing kanamycin (25 mg/L). The selected primary strains were subjected to a second cross-over. The gene introduction in the finally transformed strains was determined by carrying out PCR using primer pairs of SEQ ID NOS: 6 and 13.

The IMP productivities of CJI9088 and the prepared strains, CJI9088_impE1(WT)2X and CJI9088_impE1E2(WT)2X, were evaluated. After completion of the culture, the abilities to produce IMP was measured by HPLC, and the results of the culture are shown in Table 9 below.

TABLE 9

| Strain | IMP (g/L) |
|---|---|
| CJI9088 | 0.52 |
| CJI9088_impE1(WT) 2X | 0.68 |
| CJI9088_impE1E2(WT) 2X | 0.87 |

As a result of confirming the accumulated IMP amount in the medium, it was found that the abilities to produce IMP was increased by up to 67% compared to that of the parent strain, CJI9088. From the results above, it was confirmed that the abilities to produce IMP can be increased by enhancing the activity of the protein (ImpE) of the present disclosure, which exports IMP.

From the foregoing, those skilled in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A microorganism of the genus *Corynebacterium* producing 5' comprising a 5'-inosine monophosphate export protein consisting of the amino acid sequence of SEQ ID NO: 1 or 2, wherein said 5'-inosine monophosphate export protein has enhanced activity as compared to a microorganism without said 5'-inosine monophosphate export protein, and wherein said microorganism produces 5'-inosine monophosphate.

2. The microorganism according to claim 1, wherein the microorganism of the genus *Corynebacterium* producing 5'-inosine monophosphate is *Corynebacterium stationis*.

3. A method for preparing 5'-inosine monophosphate, comprising culturing the microorganism of the genus *Corynebacterium* of claim 1 in a medium; and recovering 5'-inosine monophosphate from the microorganism or medium.

4. The method according to claim 3, wherein the microorganism of the genus *Corynebacterium* producing 5'-inosine monophosphate is *Corynebacterium stationis*.

* * * * *